United States Patent [19]
Pankratz et al.

[11] Patent Number: 5,876,935
[45] Date of Patent: Mar. 2, 1999

[54] LUMINESCENT SPECIFIC BINDING ASSAY

[75] Inventors: Thomas John Pankratz, Newark; Richard Wayne Stout, Wilmington, both of Del.

[73] Assignee: Dade Behring Inc., Deerfield, Ill.

[21] Appl. No.: 780,307

[22] Filed: Jan. 8, 1997

[51] Int. Cl.$^6$ ............... C12Q 1/68; G01N 33/532; G01N 33/553
[52] U.S. Cl. ............... 435/6; 435/7.5; 435/7.93; 435/7.94; 436/518; 436/526
[58] Field of Search .................. 435/6, 7.5, 7.92, 435/7.93, 7.94, 968; 436/518, 526

[56] References Cited

U.S. PATENT DOCUMENTS

| | | |
|---|---|---|
| 4,380,580 | 4/1983 | Boguslaski et al. . |
| 4,401,765 | 8/1983 | Craig et al. . |
| 4,604,364 | 8/1986 | Kosak . |
| 4,661,408 | 4/1987 | Lau et al. . |
| 5,096,809 | 3/1992 | Chen et al. . |
| 5,162,227 | 11/1992 | Cormier . |
| 5,200,313 | 4/1993 | Carrico . |
| 5,288,623 | 2/1994 | Zenno et al. . |
| 5,360,728 | 11/1994 | Prasher . |
| 5,369,006 | 11/1994 | Obsansky . |
| 5,461,136 | 10/1995 | Krutak et al. . |
| 5,486,455 | 1/1996 | Stults . |
| 5,521,319 | 5/1996 | Huber et al. . |

FOREIGN PATENT DOCUMENTS

| | | |
|---|---|---|
| 0 137 515 A2 | 4/1985 | European Pat. Off. . |
| 0 372 352 A2 | 6/1990 | European Pat. Off. . |
| 0 724 156 A1 | 7/1996 | European Pat. Off. . |
| 0 768 530 A1 | 4/1997 | European Pat. Off. . |
| WO 89/11102 | 11/1989 | WIPO . |
| WO 93/19366 | 9/1993 | WIPO . |

OTHER PUBLICATIONS

Stults, N.L. et al., "Use of Recombinant Biotinylated Aequorin in Microtiter and Membrane–Based Assays: Purification of Recombinant Apoaequorin from *Escherichia coli*," *Biochemistry*, vol. 31, No. 5, pp. 1433–1442 (1992).

Sgoutas, D.S. et al., "AquaLite® Bioluminescence Assay of Thyrotropin in Serum Evaluated," *Clin. Chem.*, vo.. 41, No. 11, pp. 1637–1643 (1995).

Rivera, H.N. et al., "A Bioluminescent Immunoassay for HCG that Uses Recombinant Aequorin (AquaLite®) as the Label," *Clin. Chem.*, vol. 41, No. 6, p. S42 (1995).

SeaLite Sciences Technical Report No. 8, "Stability of AquaLite®: Lyophilized and in Solution," SeaLite Sciences, Inc., Bogart, GA, pp. 1–11, (1994).

SeaLite Sciences Technical Report No. 5, "A Third Generation, Supersensitive TSH Assay Using Recombinant Aequorin," SeaLite Sciences, Inc., Bogart, GA (undated).

Smith, D.F. et al., "A Microplate–Based Biolumnescent Immunoassay for TSH Using Recombinant Aequorin (AquaLite®)," *Clin. Chem.*, vol. 41, No. 6, p. S84 (1995).

Patel, M.T. et al., "A Bioluminescent Immunoassay for FSH that Uses Recombinant Aequorin (AquaLite®) as the Label," *Clin. Chem.*, vol. 41, No. 6, p. S33 (1995).

Rivera, H.N. et al., "A Bioluminescent Immunoassay (BIA) for the Determination of Human Chorionic Gonadotropin (hCG) Using the Recombinant Photoprotein, Aequorin," *Clin. Chem.*, vol. 40, No. 6, p. 1035 (1994).

Smith, D.F. et al., "Use of Recombinant Aequorin in Solid Phase Assays of Antigens and Enzymes," *Clin. Chem.*, vol. 37, No. 6, p. 1029 (1991).

Rivera, H. et al, SeaLite Sciences Technical Report No. 6,"AquaLite®–Streptavidin for Supersensitive TSH Assays in Microtiter Plates and Coated Tubes," SeaLite Sciences, Inc., Bogart, GA, pp. 1–6 (undated).

SeaLite Sciences Technical Report No. 7, "AquaLite® TSH in a High vol., Large Hospital or Reference Laboratory Environment," SeaLite Sciences, Inc., Bogart, GA (undated).

Hart, R.C. et al., "A Bioluminescent Assay Capable of Detecting <2 Attomoles of hTSH in Serum Using the Recombinant Calcium–Triggered Photoprotein, Aequorin," *Chemiluminescent and Bioluminescent Assays*, pp. 320–323 (1992).

Birkmeyer, et al.; *Clin. Chem*; Application of Novel Chromium Dioxide Magnetic Particles to Immunoassay Development; 33/9: 1543–1547; (1987).

*Primary Examiner*—Donna C. Wortman
*Attorney, Agent, or Firm*—Leland K Jordan; Michael G Sullivan; Lois K Ruszala

[57] ABSTRACT

A luminescent specific binding assay method is used for detecting an analyte in whole blood. The assay is a heterogeneous sandwich or competitive assay in which a first binding reagent is labeled with a luminescent photoprotein and an immobilized second binding reagent serves as a capture reagent. The luminescent photoprotein, upon activation, emits light which may be detected by a luminescence detector. The assay is rapid, sensitive and may be performed on small sample volumes.

13 Claims, 1 Drawing Sheet

LUMINESCENT SPECIFIC BINDING ASSAY

BACKGROUND OF THE INVENTION

1. Field of the Invention

This invention relates to methods and kits for performing specific binding assays. More particularly, the invention relates to a specific binding assay in which a luminescent substance, preferably the photoprotein, aequorin, is employed as a label. The luminescent specific binding assay of this invention is useful for determining the presence of various analytes in whole blood.

2. Description of the Background Art

Specific binding assay methods are used for quantitative and qualitative determinations of a wide variety of substances, generally referred to herein as "analytes." These substances may be large complex molecules, such as proteins, viruses, viral antigens, bacterial cells, cell surface receptors, enzymes, hormones, polysaccharides, glycoproteins, lipoproteins and the like, or small haptenic molecules, such as peptides, certain hormones, therapeutic drugs, drugs of abuse and the like.

These assays take advantage of specific binding reactions that occur between biological molecules. The specific binding reaction most commonly used is that which occurs between an antibody and an antigen. In that case, the specific binding assay is referred to as an immunoassay. Reactions between other binding pairs may also be employed. For example, interactions between enzymes and substrates, between hormones and receptors, and between complementary strands of nucleic acids, have been used for this purpose. Other binding reactions, such as those between avidin and biotin and between immunoglobulins and immunoglobulin binding proteins (e.g., Protein A and Protein G) have also been used advantageously in specific binding assays.

Specific binding assays may be configured in a variety of formats. For example, such assays may be competitive or sandwich assays. They may be homogeneous or heterogenous, and they may be sequential or simultaneous. In most specific binding assays, at least one of the members of the binding pair that participate in the specific binding reaction is labeled. The label provides a means for detecting and quantifying the reaction product. Radioimmunoassays employ a binding pair member (e.g., an antigen) that contains a radioactive isotope. In enzyme immunoassays, one of the binding pair members is labeled with an enzyme. The enzyme may, in turn, react with a substrate that produces a detectable signal, such as a color change.

Luminescent specific binding assays utilize any of a variety of chemiluminescent and bioluminescent labels. One such assay utilizes a photoprotein, known as aequorin, as the label. Aequorin is a high-affinity calcium ion-binding protein responsible for the bioluminescence of the jellyfish, *Aequorea Victoria*. Native aequorin is a photoprotein consisting of a single polypeptide chain of MW 21,000 daltons, containing one mole each of tightly bound coelenterate luciferin and oxygen. This complex is stable in the absence of calcium ions, and light emission is initiated upon the binding of three moles of calcium ions per mole of aequorin. In the presence of calcium ions, aequorin catalyzes the oxidation of luciferin to oxyluciferin with a concomitant flash of blue light ($\lambda_{max}$=469 nm) which persists for approximately ten seconds. See, Stults, N. L. et al., *Biochemistry* 31, 1433–42 (1992) and references cited therein.

Aequorin can be isolated from Aequorea tissue. In addition, it can be produced by recombinant DNA techniques. See Cormier, M. J., U.S. Pat. No. 5,162,227 and Zenno. S. et al., U.S. Pat. No. 5,288,623. Modified forms of apoaequorin having enhanced bioluminescence properties have also been produced by recombinant DNA procedures. See Prasher, D., U.S. Pat. No. 5,360,728. As used herein, the term "aequorin" includes the native and recombinant forms of the photoprotein, as well as its modified forms as described in the aforementioned Prasher patent.

Other photoproteins are known that can be used as labels in specific binding assays. Such photoproteins include obeln, mnemiopsin, berovin, pholasin, luciferases and photoproteins isolated from Pelagia, Cypridina and ostracods.

Most specific binding assays are designed for analyzing biological fluids, such as blood or urine, for analytes of biological significance. When the goal of a specific binding assay is to determine the presence of a substance in whole blood, typically the sample must be pretreated to remove cellular components and hemoglobin, which can interfere with the assay. Specific binding assays are usually performed on the serum component of whole blood. Alternatively, whole blood assays have been designed to provide for a filtration or absorption step preceding the specific binding assay to minimize interference from cellular components and hemoglobin. See A Chen, F. M., U.S. Pat. No. 5,096,809. Herein, the terms "blood" and "whole blood" are used interchangeably and are defined to mean a homogeneous liquid that circulates through the body's cardiovascular channels that has not been treated to achieve any separation of its components, these components essentially comprising corpuscles, plasma, serum, and fibrin.

Often, it would be highly desirable to perform a specific binding assay directly on whole blood. Lower sample volumes are needed for assays performed directly on whole blood, because sample losses resulting from pretreatment steps are avoided. Moreover, the time for an assay to be conducted can be minimized if pretreatment steps are eliminated. In emergency room or operating room environments, particularly involving pediatric patients, these factors can be of critical importance.

SUMMARY OF THE INVENTION

In accordance with this invention, a luminescent specific binding assay method involves the steps of (a) obtaining a sample of whole blood which contains or is suspected of containing an analyte, (b) combining with the sample a first binding reagent that is capable of binding to the analyte; said first binding reagent being labeled with a luminescent molecule, (c) contacting the sample with a second binding reagent that is capable of binding to the analyte and forming a complex with the analyte or the analyte bound to the first binding reagent, said second binding reagent being immobilized on a solid support; (d) separating the solid support from the sample so as to remove from the sample the complex of the first binding reagent, the analyte and the second binding reagent; (e) activating the luminescent label in the solid support-free sample or the luminescent label that bound to the solid support; and (f) determining the presence of analyte in the sample by detecting the light emitted from the activated luminescent label.

An alternative embodiment of the specific binding assay method utilizes a competitive assay format in which the first binding reagent is not used. In this embodiment, the whole blood sample is combined with a known amount of labeled analyte which has been labeled with a luminescent label. Labeled and unlabeled analyte compete with the immobilized second binding reagent, and the amount of labeled analyte that is captured by the second binding reagent is inversely proportional to the amount of unlabeled analyte present in the sample.

In a particular embodiment, the specific binding assays of this invention utilize aequorin as the luminescent label and utilize magnetic particles as the solid support.

In another embodiment, the invention relates to luminescent assay kits which contain reagents employed in the assay methods described herein.

DETAILED DESCRIPTION OF THE INVENTION

Figure 1:
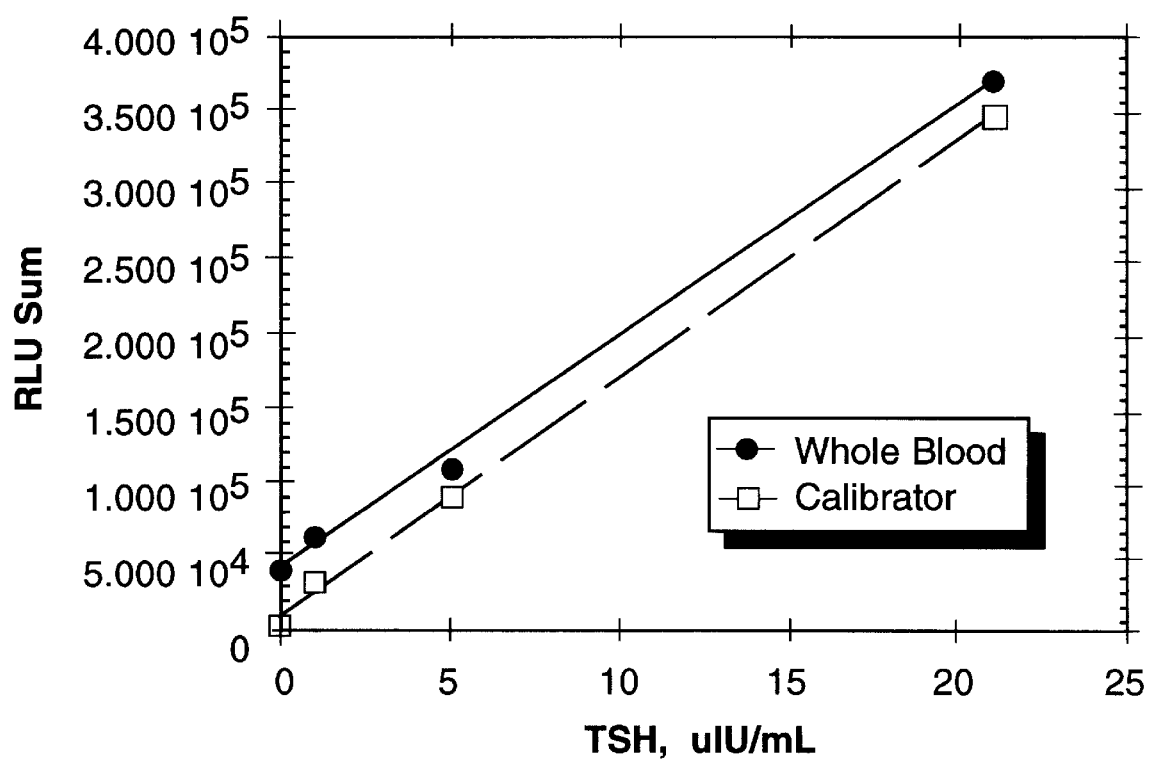
FIG. 1 depicts calibration curves resulting from an assay method according to this invention showing the light emission as a function of TSH concentration in both whole blood-free standard solutions and in the presence of whole blood.

The luminescent binding assay method of this invention is used for the determination of analytes in whole blood samples without pretreatment steps. The assay is sensitive and can provide rapid and accurate results, even when sample volumes are small.

The luminescent specific binding assay is a heterogeneous assay that may be conducted in the sandwich or competitive format. In the sandwich format, it employs a first binding reagent, e.g., an antibody, that has been labeled with a luminescent substance and a second binding reagent, e.g., a second antibody, that serves as a capture reagent. In the sandwich format, both the first and second binding reagents are capable of binding simultaneously to the analyte of interest. The second binding reagent is immobilized on a solid support. The immobilization may be accomplished by bonding the second binding reagent and the solid support either directly or through at third binding reagent that is immobilized on the solid support. When the latter embodiment is employed, the reactions of the first and second binding reagents with the analyte may occur before the solid support is introduced to the sample, in which case, those reactions behave substantially in accordance with solution reaction kinetics. Alternatively, all of the components may be added at the same time, in which case the binding reactions occur simultaneously.

The complex formed by the reaction of the first and second binding reagents with the analyte is separated from unbound labeled binding reagent by separating the solid support from the sample mixture. In a preferred embodiment of this invention, the second binding reagent is immobilized on magnetic particles, either directly or indirectly through an immobilized third binding reagent. The separation step may involve either removal of the particles from the sample or localization of the particles within the sample to allow the detection of luminescence.

After separation or isolation of the immobilized complex, the luminescent label is activated to cause the emission of light. Light emission may be detected either from the sample or from the complex immobilized on the solid support or both.

The labeled first binding reagent is prepared by conjugating a luminescent label to a binding reagent. The binding reagent may, for example, be a polyclonal, monoclonal or complementary determining region-grafted antibody or a binding fragment thereof, e.g., Fab, Fab' or F(ab')$_2$ fragment, or a synthetic single-chain antibody. Alternatively, the binding reagent may be a nucleic acid (RNA or DNA) strand or other molecule that participates in a specific binding reaction, e.g., a hormone, a receptor, an enzyme, a binding protein such as folate binding protein or intrinsic factor, a substrate, an immunoglobulin binding protein, such as protein A or protein G, and the like. The first binding reagent has a binding affinity for the analyte of interest.

In the competitive assay format, the first binding reagent is not used. The immobilized second binding reagent which is capable of binding with the analyte of interest is combined with the sample or calibration standard and a fixed amount of analyte that has been labeled with a luminescent molecule. Unlabeled analyte in the sample or standard competes with labeled analyte for the immobilized binding reagent. The amount of labeled analyte that binds to the immobilized binding reagent is inversely proportional to the amount of analyte in the sample or standard. As in the sandwich format, the second binding reagent may be bound directly to the solid support or may be capable of binding to a third binding reagent that is immobilized on the solid support as described above.

The luminescent label which is conjugated to the first binding reagent (or the analyte, in the case of a competitive assay format) may be any luminescent compound that retains its ability to emit light when conjugated to a binding reagent. The preferred luminescent label is aequorin. When exposed to calcium ion, aequorin emits blue light with a high quantum yield at a wavelength where the absorbance by whole blood is relatively low. The use of aequorin as the luminescent label permits the design of sensitive whole blood assays.

The aequorin used in the present invention may be native aequorin isolated from jellyfish tissue or may be recombinant (synthetic) aequorin. In addition, it may be a modified aequorin having enhanced bioluminescent properties.

Aequorin can be conjugated to antibodies, nucleic acids, various analytes and other binding reagents without substantially interfering with the luminescence characteristics of the compound. Procedures for conjugating aequorin and related photoproteins to binding reagents are described by Stults, M. L., U.S. Pat. No. 5,486,455, the disclosure of which is incorporated herein by reference. Other conjugation procedures known to those skilled in the art also may be used.

In addition to aequorin, other luminescent labels that may be employed in the luminescent specific binding assay of the present invention include other photoproteins, such as obelin, mnemiopsin, berovin; pholasin, luciferases, and photoproteins isolated from Pelagia, Cypridina and ostracods and non-proteinaceous luminescent compounds, such as 2,3-dihydro-1,4phthalayinediones, acridinium ester, acridinium sulfonalamide, luciferins, luminol, 1-2-dioxetanes, cyclic hydrazides, europium chelates and phenol derivatives.

As discussed above, in either the sandwich or competitive format, the second binding reagent may be immobilized on a solid support either through a direct bond, or through an affinity for an immobilized third binding reagent. In the latter embodiment, the affinity of the second binding reagent for the third binding reagent may take any of a variety of forms. For example, if the second binding reagent is an immunoglobulin, the immobilized third binding reagent may be an immunoglobulin binding protein, such as Protein A or Protein G or an anti-immunoglobulin antibody. Alternatively, the second binding reagent may be labeled with an antigen or hapten and the third binding reagent may be an antibody to that antigen or hapten. For example, the second binding reagent may be biotinylated in which case the immobilized third binding reagent then is avidin or streptavidin. Conversely, the second binding reagent may be conjugated with avidin or streptavidin in which case the immobilized third binding reagent is biotin. Biotin forms a strong, non-covalent bond with avidin or streptavidin. Procedures for biotinylating antibodies, proteins and nucleic acids are well-known in the art. See e.g. Huber E. et al., U.S. Pat. No. 5,521,319 and Carrico, R. J., U.S. Pat. No. 5,200,313, the disclosures of which are incorporated herein by reference.

The solid support on which the second binding reagent is immobilized may be any of the wide variety of solid supports known for use in heterogenous immunoassays. Microparticles are preferred for use as the solid support, because their high surface area improves the efficiency and kinetics of the capture step. Latex particles of the type disclosed by Craig, et al., U.S. Pat. No. 4,401,765 and magnetic particles, such as those available from Bangs Laboratories, Inc., Fishers, Ind., 46038-2886, USA, are preferred. Cortex particles, available from Cortex Biochem, San Leandro, Calif., may be used in an alternative embodiment. Stabilized chromium dioxide particles described in U.S. Pat. No. 4,661,408 issued Apr. 28, 1987, incorporated herein by reference, may also be used. These particles, and their use in immunoassays are described by Obzansky, D. M., U.S. Pat. No. 5,369,006, incorporated herein by reference. The Obzansky patent describes procedures for immobilizing binding reagents, such as streptavidin on the surface of the chromium dioxide particles.

Magnetic particles are preferred for the practice of this invention, because mixing and separation steps can be conveniently and rapidly accomplished by application of a strong magnetic field. For example, it has been found that the present assay functions particularly well when magnetic particles are caused to "swim" back and forth across a reaction vessel by alternately applying a magnetic field to opposite sides of the vessel. Following separation of the complex from the solution, the luminescent label is activated and the light emission is detected. Light emission either of the luminescent label immobilized on the solid support or of the solution from which the solid support has been separated may be measured. The amount of analyte in the sample can be quantified by comparing the level of emitted light to a standard calibration curve.

While the specific binding assay of this invention may be formatted in a variety of different ways, in a preferred embodiment, the first binding reagent is an aequorin-labeled monoclonal antibody that is capable of binding to the analyte. The second binding reagent is a biotinylated monoclonal antibody that is capable of binding to the analyte. The solid support is preferably streptavidin-coated superparamagnetic microspheres, such as those available from Bangs Laboratories, Inc., Fishers, Ind., 46038-2886, USA under the stock no. C0008200RN. The reaction can be performed in a vessel such as a test tube or a microtiter well. The reaction is initiated by combining a whole blood sample or calibrator with appropriate amounts of the first binding reagent and the second binding reagent in a suitable buffer solution. The sample is incubated for a sufficient length of time to permit the immunoreaction to occur. The streptavidin-coated magnetic particles are then added to the sample, and the mixture is agitated and incubated to allow binding of the immunocomplex to the magnetic particles. The particles are separated by application of a magnetic field, washed and resuspended. Sufficient calcium ions are added to cause the emission of light by the luminescent aequorin label. The light emitted is detected by a luminescence detector, and the reading is correlated to the concentration of the analyte by comparison to a calibration curve.

It will be appreciated by those skilled in the art that the specific binding assay of this invention may be performed manually or is readily adaptable to automated equipment. The order of addition of reagents is not critical, provided that the various binding reactions are allowed to proceed to a point that a qualitative or quantitative measurement, as desired, can be obtained.

The invention is further illustrated by the following examples, which are not intended to be limiting.

EXAMPLE 1

Bioluminescent Assay For TSH

Styrene microtiter plate wells were pre-soaked overnight at room temperature with a buffer composed of phosphate-buffered saline ("PBS") having 140 mM sodium chloride, 2.7 mM potassium chloride, 10 mM sodium phosphate, pH 7.4 with added 10 mM magnesium chloride, 10 mM EGTA, 6.1% sodium azide and 5% bovine serum albumin ("BSA"). The microtiter plate wells were drained and air-dried before use. The following was added with mixing to a microtiter well: 0.1 ML of a TSH calibrator containing 21 mIU/L TSH, 50 nanograms of biotinylated mouse monoclonal antibody to TSH (Boehringer Mannheim, Indianapolis, Ind., USA, cat. No. 1367978 (clone A8TSH)) and 9 nanograms of aequorin labeled monoclonal antibody to TSH (obtained from SeaLite Sciences, Inc. Norcross, Ga., USA, lot. no. 46-145, prepared by conjugating aequorin to a mouse monoclonal antibody to TSH produced from done 057-11003 obtained from OEM Concepts Inc., (Toms River, N.J.) in 20 $\mu$l of buffer (1M potassium chloride 10 mM tris, pH 7.5, 10 mM magnesium chloride, 10 mM EGTA, 0,1% sodium azide, and containing 0.1% BSA). This solution was incubated at 37 C for 15 minutes. Twenty microliters (22.5 microgram) of strepavidin coated superparamagnetic microspheres (Bangs Laboratories, Inc., Fishers, Ind., USA, stock code C0008200RN) in PBS with added 0.1% BSA, and 0.1% Triton X-100 were then added to the solution with mixing. The mixture was incubated at 37 C for 5 minutes. The particles were then separated by application of a quadrapole magnetic field. The particles were washed four times with 100 microliters of a wash buffer containing PBS pH 7.4, 10 mM magnesium chloride, 10 mM EGTA, 0.1% sodium azide and 0.05% Tween 20. The particles were then resuspended in 100 microliters of the same wash buffer. One hundred microliters of 0.1M $CaCl_2$ was injected into the particle suspension with mixing. Light emission was measured for ten seconds using a Dynatech ML 3000 luminescence detector.

The foregoing procedure was repeated with additional calibrator solutions, whole blood samples, and spiked whole blood samples spiked with TSH concentrations of 1, 5 and 21 mIU/L. The reading from the luminescence detector was plotted against TSH concentration and the response was found to be linear throughout the range that was tested. The data are set forth in Table I below and the resulting calibration curves are shown in FIG. 1 where aequorin response is provided as a function of TSH concentration in whole blood and calibrator. The difference between the calibrator and spiked whole blood values are due to endogenous normal TSH in the whole blood sample of 1.3 mIU/L.

TABLE 1

| | TSH µIU/mL | | | |
|---|---|---|---|---|
| | 0 | 1 | 5 | 21 |
| | Luminescence Counts | | | |
| Calibrator: | 1934 | 28141 | 101307 | 390408 |
| | 2121 | 38324 | 81215 | 344986 |
| | 1796 | 27716 | 89634 | 310261 |
| Mean: | 1941 | 31394 | 90719 | 348552 |
| Std. Dev.: | 176 | 6005 | 10089 | 40192 |
| % CV: | 9.1 | 19.1 | 11.1 | 11.5 |
| Whole Blood: | 37643 | 65008 | 113649 | 306018 |
| | 37933 | 63562 | 98674 | 435896 |
| | 42230 | 59760 | 119011 | 376953 |
| Mean: | 39269 | 62777 | 110445 | 37956 |
| Std. Dev.: | 2568 | 2710 | 10540 | 65031 |
| % CV: | 6.5 | 4.3 | 9.5 | 17.4 |

TABLE 2

| | MCKMB ng/mL: | |
|---|---|---|
| | 0 | 329 |
| | Luminescence Counts | |
| Calibrator: | 263 | 133514 |
| | 321 | 132782 |
| | 836 | 117215 |
| Mean: | 473 | 127837 |
| Std. Dev.: | 315 | 9206 |
| % CV: | 66.6 | 7.2 |
| Whole Blood: | 591 | 126315 |
| | 475 | 120287 |
| | 298 | 107301 |
| Mean: | 591 | 126315 |
| Std. Dev.: | 147 | 9716 |
| % CV: | 32.5 | 8.2 |

EXAMPLE 2

Bioluminescence Assay For Creatine Kinase, MB Isoenzyme (CKMB)

In a similar manner to Example 1, styrene microtiter plate wells were pre-soaked overnight at room temperature with a buffer composed of phosphate-buffered saline ("PBS") having 120 mM sodium chloride, 2.7 mM potassium chloride, 10 mm. sodium phosphate, pH 7.4, with added 10 mM magnesium chloride, 10 mM EGTA, 0.1% sodium azide and 5% bovine serum albumin ("BSA"). The microtiter plate wells were drained and air-dried before use. The following was added with mixing to a microtiter well: 25 microliters of a CKMB calibrator containing 329 ng/mL CKMB, 100 nanograms of biotinylated mouse monoclonal antibody to CKMB (Dade Chemistry Systems Inc. part number 735322.312) and 20 nanograms of aequorin labeled F(ab')2 fragment of a monoclonal antibody to CKMB (Dade Chemistry Systems Inc. part number 735322.305) in 20 microliters of buffer (1M potassium chloride, 10 mM tris, pH 7.5, 10 mM magnesium chloride, 10 mM EGTA, 0.1% sodium azide, 0.1% BSA, and 80 mL of PBS with added 10 mM magnesium chloride, 10 mM EGTA, and 0.05% Tween 20. This solution was incubated at 37° C.. for 15 minutes. Twenty microliters (22.5 microgram) of streptavidin coated superparamagnetic microspheres (Bangs Laboratories, Inc., Fishers, Ind., USA, stock code C0009000RN) in PBS with added 0.1% BSA and 0.05% Triton X-100 were then added to the solution with mixing. The mixture was incubated at 37° C. for 5 minutes. The particles were then separated by application of a quadrapole magnetic field. The particles were washed four times with 100 microliters of a wash buffer containing PBS pH 7.4, 10 mM magnesium chloride, 10 mM EGTA, 0.1% sodium azide and 0.05% Tween 20. The particles were then resuspended in 100 microliters of the same wash buffer. One hundred microliters of 0.1M calcium chloride was injected into the particle suspension with mixing. Light emission was measured for ten seconds using a Dynatech ML 3000 luminescence detector. The foregoing procedure was repeated with the addition of 25 uL whole blood (collected in an EDTA-containing vacuum collection tube). The procedure was repeated again with an additional calibrator containing 0 ng/mL CKMB, with and without added whole blood as above. The data are set forth in Table 2 below.

We claim:

1. A heterogenous luminescent specific binding assay method in whole blood, which comprises
   (a) obtaining a sample of whole blood which contains or is suspected of containing an analyte;
   (b) combining with the sample of whole blood a first binding reagent that is capable of binding to the analyte, said first binding reagent being labeled with a luminescent photoprotein, aequorin, which, upon activation, emits light;
   (c) contacting the sample with a second binding reagent that is capable of binding to the analyte, said second binding reagent being immobilized on a solid support;
   (d) allowing said first and second binding reagents to react with the analyte present in the sample under binding conditions to produce a complex;
   (e) separating the complex from the sample by separating the solid support from the sample;
   (f) activating the luminescent photoprotein label in the solid support-free sample or in the complex that bound to the solid support; and
   (g) determining the presence of analyte in the sample by detecting the light emitted from the activated luminescent photoprotein label.

2. A heterogeneous specific binding assay method in whole blood, which comprises
   (a) obtaining a sample of whole blood which contains or is suspected of containing an analyte;
   (b) combining with said sample of whole blood a known quantity of the analyte which has been labeled with a luminescent photoprotein, aequorin, which, upon activation, emits light;
   (c) contacting the sample with a second binding reagent that is capable of binding to the analyte, said binding reagent being immobilized on a solid support;
   (d) allowing said second binding reagent to react with the labeled and unlabeled analyte to produce complexes;
   (e) separating the complexes from the sample by separating the solid support from the sample;
   (f) activating the aequorin label in the solid support-free sample or in the complex that bound to the solid support; and
   (g) correlating the light emission from the sample with the presence of analyte in the sample.

3. The method of claims 1 or 2, wherein the second binding reagent is bound directly to the solid support.

4. The method of claims 1 or 2, wherein the second binding reagent has the capability of binding both the analyte and a third binding reagent that is immobilized on the solid support, the assay method further comprising contacting the sample with the solid support that has immobilized thereon the third binding reagent.

5. The method of claim 4, in which the aequorin label is activated to emit light by the addition of an activating amount of calcium ions.

6. The method of claim 4, in which the solid support comprises magnetic microparticles.

7. The method of claim 6, in which the separation defined in step (e) is achieved by application of a magnetic field, and the separated magnetic particles are resuspended in a solution, the luminescent label in the particle suspension is activated, and light emission is detected.

8. The method of claim 4 in which each of the first and second binding reagents is an antibody or an immunoreactive fragment thereof.

9. The method of claim 8, in which the second binding reagent is biotinylated and the third binding reagent is avidin or streptavidin.

10. The method of claim 4, in which each of the first and second binding reagents is a monoclonal antibody.

11. The method of claim 4, in which each of the first and second binding reagents is a nucleic acid.

12. The method of claim 11, in which the second binding reagent is biotinylated and the third binding reagent is avidin or streptavidin.

13. The method of claim 4, in which the second binding reagent is biotinylated and the third binding reagent is avidin or streptavidin.

* * * * *